United States Patent [19]

Goldstein

[11] Patent Number: 5,037,842

[45] Date of Patent: Aug. 6, 1991

[54] OXA- AND THIAZOLIDINEDIONE HYPOGLYCEMIC AND HYPOCHOLESTEROLEMIC AGENTS

[75] Inventor: Steven W. Goldstein, Mystic, Conn.

[73] Assignee: Pfizer Inc., New York, N.Y.

[21] Appl. No.: 533,615

[22] Filed: Jun. 5, 1990

[51] Int. Cl.⁵ ............................................ C07D 263/54
[52] U.S. Cl. .................... 514/375; 514/369; 548/183; 548/217; 548/224
[58] Field of Search ....................... 548/217, 224, 183; 514/375

[56]  References Cited

U.S. PATENT DOCUMENTS

| | | | |
|---|---|---|---|
| 4,340,605 | 7/1982 | Kawamatsu et al. | 548/183 |
| 4,550,172 | 10/1985 | Musser | 548/217 |
| 4,689,336 | 8/1987 | Schnur | 514/376 |
| 4,703,052 | 10/1987 | Eggler et al. | 548/183 |
| 4,753,956 | 6/1988 | Schnur | 548/217 |
| 4,775,687 | 10/1988 | Meguro et al. | 548/183 |
| 4,791,125 | 12/1988 | Clark | 548/183 |
| 4,948,900 | 8/1990 | Iijima | 548/183 |

FOREIGN PATENT DOCUMENTS

| | | | |
|---|---|---|---|
| 2234085 | 10/1987 | Japan | 548/183 |
| 89/08650 | 9/1989 | PCT Int'l Appl. | 548/183 |

Primary Examiner—Donald G. Daus
Attorney, Agent, or Firm—Peter C. Richardson; J. Trevor Lumb; James M. McManus

[57] ABSTRACT

A series of 5-(4-[2-substituted benzoxazolylmethoxy]-benzyl)oxa- and thiazolidine-2,4-diones as antidiabetic and cholesterol lowering agents.

9 Claims, No Drawings

OXA- AND THIAZOLIDINEDIONE HYPOGLYCEMIC AND HYPOCHOLESTEROLEMIC AGENTS

BACKGROUND OF THE INVENTION

The present invention relates to certain compounds of formula (I), depicted below, having utility as hypoglycemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more sever cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

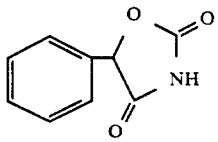

in which the phenyl ring is generally mono- or multisubstituted in the ortho/meta positions. Notably, with the exception of the 4-fluorophenyl analog, the parasubstituted derivatives are either inactive or possess a low level of hypoglycemic activity. Schnur, U.S. Pat. Nos. 4,332,952 and 4,342,771 further disclose a variety of similar oxazolidinedione hypoglycemic agents which are alternatively substituted at the 5-position with a heterocyclic group. These include certain furan, thiophene, pyrrole and pyridine derivatives.

Schnur, U.S. Pat. No. 4,617,312 discloses hypoglycemic thiazolidinediones of the formula

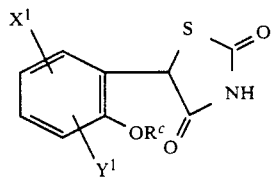

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen. Shoda et al. (Chem. Pharm. Bull., 30, 3563 (1982) describe the preparation of a series of 5-[4-(2-methyl-2-phenylpropoxy)benzyl]thiazolidine-2,4-diones as antidiabetic agents.

Kawamatsu et al., U.S. Pat. No. 4,340,605, disclose hypoglycemic compounds of the formula

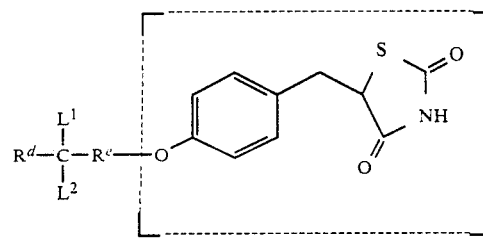

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. Based on the lack of hypoglycemic and plasma triglyceride lowering activity of certain non-ether analogs, it has been suggested that the boxed portion of the structural formula, including the ether oxygen, represents an essential feature for useful activity in this series of compounds; Sohda et al., Chem. Pharm. Bull. Japan, Vol. 30, pp. 3580–3600 (1982).

Sohda et al. also describe the compound of the formula

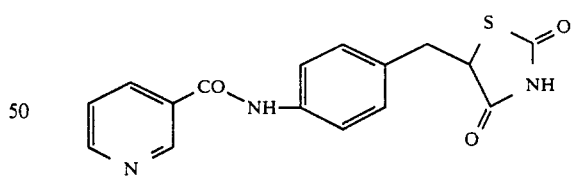

as having weak hypoglycemic and plasma triglyceride lowering activity.

Eggler et al., U.S. Pat. No. 4,703,052, discloses hypoglycemic thiazolidinediones of the formula

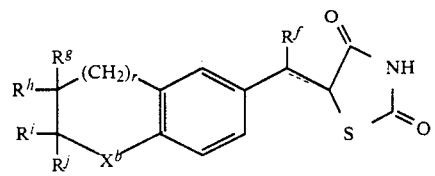

where the dotted line represents an optional bond, $R^f$ is H, methyl or ethyl, $X^b$ is O, S, SO, $SO_2$, $CH_2$, CO, CHOH or NR$^k$, R$^k$ is H or an acyl group and the numerous definitions of R$^g$, R$^h$, R$^i$ and R$^j$ include R$^g$, R$^h$ and R$^i$ as hydrogen or methyl and R$^j$ as optionally substituted phenyl, benzyl, phenethyl or styryl.

Meguro et al., U.S. Pat. No. 4,725,610 disclose a series of hypoglycemic thiazolidinediones of the formula

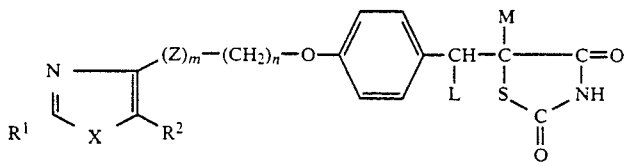

EP 283,035A and EP 299,620A describe benzoxazole and benzofuran linked thiazolidinediones as antidiabetic agents.

SUMMARY OF THE INVENTION

The present invention relates to compounds of the formula

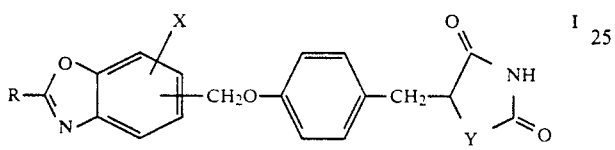

or a pharmaceutically acceptable base salt thereof wherein R is alkyl having one to six carbon atoms, cycloalkyl having one to six carbon atoms, furyl, thienyl, phenyl or substituted phenyl wherein said substituent is alkyl of one to three carbon atoms, methoxy, trifluoromethyl, chloro, or fluoro; X is hydrogen, methyl, methoxy, chloro or fluoro; and Y is O or S.

The preferred compounds are of the formula

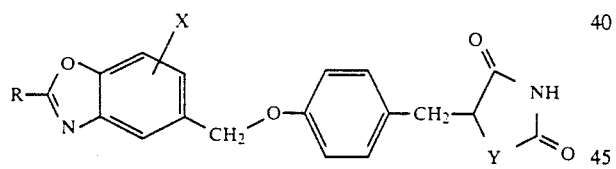

wherein X is hydrogen and Y is O.

Especially preferred within this group are the compounds where R is phenyl, 2-thienyl, 2-furyl or i-propyl.

The present invention also includes pharmaceutical compositions for use in hypoglycemic and hypercholesterolemic mammals which comprises blood sugar lowering and blood cholesterol lowering amounts, respectively, of compounds of formulae I and II with a suitable carrier.

Also included are methods for lowering blood glucose or blood cholesterol in a hyperglycemic or hypercholesterolemic mammal, respectively, which comprises administering to said mammal a blood glucose lowering or blood cholesterol lowering amount of a compound of formula I or II.

The expression "pharmaceutically-acceptable salts" is intended to define but not limited to such base salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl1,3-propanediol) and procaine.

DETAILED DESCRIPTION OF THE INVENTION

The compounds of formula I are prepared by two procedures.

The first procedure or process comprises the removal of a triphenylmethyl moiety from the 3-position of the oxazolidinedione shown as follows:

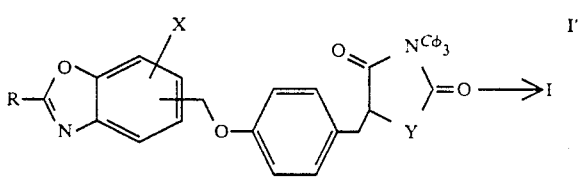

The removal of the triphenylmethyl group is achieved by treating the starting material with trifluoroacetic acid at room temperature until the reaction is complete. Reaction time is generally 30-60 minutes. The desired product is obtained by quenching the reaction mixture in water followed by extraction of the product with a water-immiscible solvent, such as ethyl acetate. The product can be purified by conventional means such as recrystallization or chromatography.

The starting reagents leading to I' can be prepared by methods herein described and comprise alkylating a phenol with a benzyl halide such as

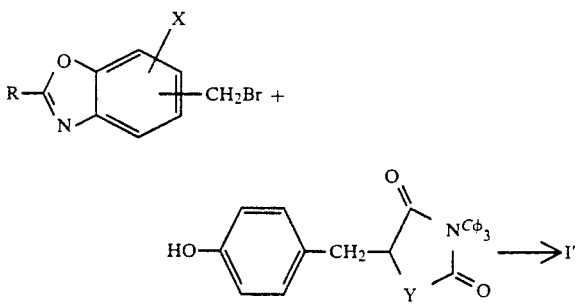

The second process leading to the subject compounds of formula I comprises the reduction of the compounds of formula I".

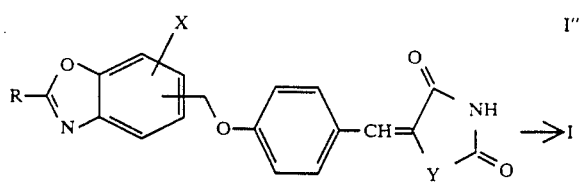

The starting olefinic products serve as intermediates for preparation of the corresponding reduced compounds of formula (I). While the reduction of these olefins may be carried out by employing a number of reducing agents which are known to reduce carbon-to-carbon double bonds, the preferred methods employ hydrogen in the presence of a noble metal catalyst, sodium amalgam in methanol, or zinc in acetic acid.

When the reduction step is carried out employing hydrogen in the presence of a noble metal catalyst, a convenient method for carrying out this transformation is to stir or shake a solution of the olefinic compound of the formula (I″) in a reaction-inert solvent under an atmosphere of hydrogen, or hydrogen mixed with an inert diluent such as nitrogen, in the presence of a sulfur resistant noble metal hydrogenation catalyst. Suitable solvents for this reaction are those which substantially dissolve the starting compound but which do not themselves suffer hydrogenation or hydrogenolysis. Examples of such solvents include ethers such as diethyl ether, tetrahydrofuran, dioxane and 1,2-dimethoxyethane; low molecular weight amides such an N,N-dimethylformamide, N-N-dimethylacetamide and N-methylpyrrolidone; and lower alkyl carboxylic acids such as formic, acetic, propionic and isobutyric acid. Especially preferred such solvents are tetrahydrofuran and acetic acid. Hydrogenation is particularly preferred when W is other than S or SO.

Introduction of the hydrogen gas into the reaction medium is usually accomplished by carrying out the reaction in a sealed vessel, containing the olefinic compound, solvent, catalyst and hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenation is generally run at a temperature of from about 0° to about 60° C., and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation, for example, palladium, platinum and rhodium. A sulfur resistant palladium catalyst is preferred because such catalysts are not readily poisoned by sulfur. The catalyst is usually present in an amount from about 0.01 to about 25 weight-percent, and preferably from about 0.1 to about 10 weight-percent, based on the olefinic compound. It is often convenient to suspend the catalyst on an inert support; a particularly convenient catalyst is palladium suspended on an inert support such as carbon.

When the hydrogenation of the methylene double bond is substantially complete, the desired product of formula (I) is then isolated by standard methods, e.g., the catalyst is recovered by filtration, the solvent evaporated and the product purified, if desired, by well known methods such as crystallization or by chromatography.

The intermediates of formula I″ are conveniently prepared by condensing the appropriate aldehyde with the 2,4-dione in the presence of a base as herein described.

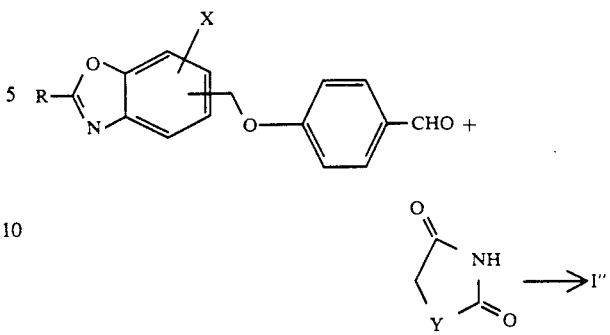

The starting reagents for the processes described herein are prepared by reactions known to those skilled in the art or are described hereinafter.

The pharmaceutically-acceptable catiońic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The present compounds of the formula (I) are readily adapted to clinical use as hypoglycemic or hypocholesterolemic agents. The activity required for the former clinical use is defined by the test for hypoglycemic effect in ob/ob mice by the following procedure:

Five to eight week old C57 BL/6J-ob/ob mice (obtained from Jackson Laboratory, Bar Harbor, Maine) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days drug (5–50 mg/kg), a positive control (50 mg/kg) of ciglitazone; U.S. Pat. No. 4,467,902; Sohda et al., Chem. Pharm. Bull , vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000 xg at room temperature. The supernatant was analyzed for glucose, for example, by the ABA 200 Bichromatic Analyzer TM , using the A-gent TM glucose UV reagent system* (hexokinase method) using 20, 60 and 100 mg/dl standards. Plasma glucose was then calculated by the equation, Plasma glucose (mg/dl) = Sample value × 5 × 1.67 = 8.35 × Sample value where 5 is the dilution factor and 1.67 is the plasma hematocrit adjustment (assuming the hematocrit is 40%). ™ A registered trademark of Abbott Laboratories, Diagnostics Division, 820 Mission Street, So. Pasadena, CA 91030.

*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Maine, are used at age 8-12 weeks, following 2-4 weeks acclimation having free access to water and standard laboratory chow. Animals are divided randomly into three groups of 6-7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9-11 a.m. for the final 5 days by oral gavage, the control group with 5 ml/kg of vehicle (0.1% aqueous methyl cellulose) and the test groups with the compound under study at a dose range of 0.1–20 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. The injectable solutions prepared in this manner can then be administered intravenously, intraperitoneally, subcutaneously, or intramuscularly, with intramuscular administration being the preferred parenteral route in man.

The present invention is illustrated by the following Examples. However, it should be understood that the invention is not limited to the specific details of these examples.

EXAMPLE 1

5-(4-[2-Isopropylbenzoxazol-5-ylmethoxy]benzyl)-oxazolidine-2,4-dione (R=i—$C_3H_7$; X=H; and Y=O)

The product of preparation F (4.73 g, 7.63 mmol) was added to trifluoroacetic acid (20 mL) and the resulting solution stirred at room temperature for 30 minutes. It was then poured into water (200 mL), neutralized with solid sodium carbonate and extracted with ethyl acetate (3×100 mL). The combined organic layers were dried with magnesium sulfate, filtered and concentrated to give a solid. Two recrystallizations from methanol gave the title compound (1.02 g, 35%) as white needles: mp 167°-169° C.

Anal. Calc'd for $C_{21}H_{20}N_2O_5$: C, 66.3; H, 5.3; N, 7.4. Found: C, 66.4; H, 5.3; N, 7.4.

EXAMPLE 2

Starting with the requisite reagents and employing the procedure of Example 1, the following compounds were prepared.

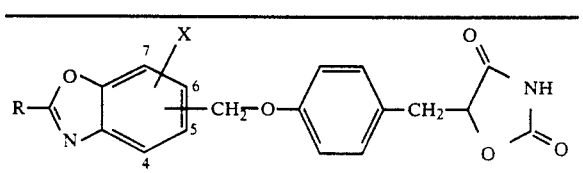

| R | X | Substitution | m.p., °C. | Yield % |
|---|---|---|---|---|
| $C_6H_5$— | H | 4 | 191–195 | 43 |
| Anal. Calc'd: | | | C, 69.6; H, 4.4; N, 6.8 | |
| Found: | | | C, 69.9; H, 4.8; N, 6.3 | |
| $CH_3$— | H | 4 | 174–176 | 57 |
| Anal. Calc'd: | | | C, 64.8; H, 4.6; N, 8.0 | |
| Found: | | | C, 64.5; H, 4.5; N, 7.8 | |
| $C_6H_5$— | H | 5 | 198–199 | 28 |
| Anal. Calc'd*: | | | C, 68.1; H, 4.3; N, 6.6 | |
| Found: | | | C, 68.4; H, 4.3; N, 6.5 | |
| $CH_3$— | H | 5 | 188–190 | 41 |
| Anal. Calc'd: | | | C, 64.8; H, 4.6; N, 8.0 | |
| Found: | | | C, 64.9; H, 4.4; N, 7.9 | |

-continued

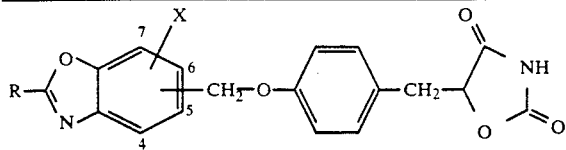

| R | X | Substitution | m.p., °C | Yield % |
|---|---|---|---|---|
| C₆H₅— | H | 6 | 180–181 | 9 |
| Anal. Calc'd: | | | C, 69.6 H, 4.4; N, 6.8 | |
| Found: | | | C, 69.3; H, 4.4; N, 6.7 | |
| CH₃— | H | 6 | 188–190 | 22 |
| Anal. Calc'd: | | | C, 64.8; H, 4.6; N, 8.0 | |
| Found: | | | C, 64.5; H, 4.5; N, 8.0 | |
| C₆H₅— | H | 7 | 211–214 | 82 |
| Anal. Calc'd: | | | C, 69.6; H, 4.4; N, 6.8 | |
| Found: | | | C, 69.0; H, 4.2; N, 7.1 | |
| CH₃— | H | 7 | 185–187 | 55 |
| Anal. Calc'd*: | | | C, 63.2; H, 4.5; N, 7.8 | |
| Found: | | | C, 63.1; H, 4.5; N, 7.5 | |
| p-CH₃C₆H₄ | H | 5 | 210–215 | 22 |
| Anal. Calc'd: | | | C, 70.1; H, 4.7; N, 6.5 | |
| Found: | | | C, 70.0; H, 4.4; N, 6.3 | |
| (2-thienyl) | H | 5 | 190–194 | 33 |
| Anal. Calc'd: | | | C, 62.8; H, 3.8; N, 6.7 | |
| Found: | | | C, 63.1; H, 3.6; N, 6.5 | |
| (2-furyl) | H | 5 | 188–190 | 58 |
| Anal. Calc'd: | | | C, 65.3; H, 4.0; N, 6.9 | |
| Found: | | | C, 65.2; H, 4.0; N, 6.9 | |
| p-CF₃C₆H₄— | H | 5 | 220–225 | 66 |
| Anal. Calc'd: | | | C, 62.2; H, 3.6; N, 5.8 | |
| Found: | | | C, 62.4; H, 3.3; N, 5.7 | |
| m-CH₃C₆H₄— | H | 5 | 180–185 | 54 |
| Anal. Calc'd: | | | C, 70.1; H, 4.7; N, 6.5 | |
| Found: | | | C, 70.4; H, 4.7; N, 6.6 | |
| i-C₃H₇ | 7-CH₃O | 5 | 109–112 | 65 |
| Anal. Calc'd: | | | C, 64.4; H, 5.4; N, 6.8 | |
| Found: | | | C, 64.8; H, 5.6; N, 6.5 | |
| (2-furyl) | 7-CH₃O | 5 | 189–192 | 39 |
| Anal. Calc'd: | | | C, 63.6; H, 4.2; N, 6.5 | |
| Found: | | | C, 63.7; H, 3.9; N, 6.3 | |
| C₆H₅ | 7-CH₃O | 5 | 216–219 | 46 |
| Anal. Calc'd: | | | C, 66.7; H, 4.7; N, 6.5 | |
| Found: | | | C, 66.8; H, 4.6; N, 6.1 | |
| (cyclohexyl) | 7-CH₃O | 5 | 136–138 | 71 |
| Anal. Calc'd: | | | C, 66.7; H, 5.8; N, 6.2 | |
| Found: | | | C, 67.0; H, 5.9; N, 6.1 | |

*calculated as ½ H₂O solvate.

EXAMPLE 3

5-(4-[2-Isopropylbenzoxazol-5-ylmethoxy]benzyl)-thiazolidine-2,4-dione (R=i—C₃H₇; X=H; and Y=S)

To a solution of the product of preparation H (445 mg, 1.13 mmol) in tetrahydrofuran (35 mL) was added sulfur resistant 10% palladium on charcoal (500 mg). The resulting suspension was shaken under 50 p.s.i. of hydrogen overnight and then filtered through celite and concentrated. Chromatographic purification on silica gel utilizing a gradient elution of hexanes to 1/1 ethyl acetate/hexanes gave the title compound (380 mg, 85%) as an oil. Recrystallization from ethyl acetate/hexanes afforded white needles: mp 128°–131° C.

Anal. Calc'd for C₂₁H₂₀N₂O₄S: C, 63.3; H, 5.1; N, 7.1.

Found: C, 63.3; H, 4.9; N, 7.0.

In a similar manner was prepared 5-(4-[2-thien2-ylbenzoxazol-5-ylmethoxy]benzyl)thiazolidine-2,4-dione, m.p. 194°–195° C. (47% yield).

Anal. Calc'd: C, 60.5; H, 3.7; N, 6.4.

Found: C, 60.2; H, 3.4; N, 6.3.

PREPARATION A

3-Triphenylmethyl-1,3-oxazolidine-2,4-dione

To a solution of 1,3-oxazolidine-2,4-dione (60.7 g, 0.600 mol) and triethylamine (60.7 g, 0.600 mol) in methylene chloride (500 mL) was added triphenylmethyl chloride (167.3 g, 0.600 mol). After 30 minutes, the thick white solid was collected by vacuum filtration, washed with water (2 L) and dried in a vacuum desicator to give the title compound (201.4 g, 96%). A portion was recrystallized from chloroform to give white plates: mp 216°–218° C.

PREPARATION B

1-Hydroxy-4-methyl-[5-(3-triphenylmethyl-1,3-oxazolyl-2,4-dione)benzene

To a suspension of the product of preparation A (150 g, 0.437 mol) and dimethylformamide (300 mL) was added methyl magnesium carbonate (437 mL, 2 M in dimethylformamide, 0.874 mol) and the reaction was then heated to 90° C. for 1.5 hours. After cooling, the above red reaction mixture was added over 10 minutes to a solution of 4-chloromethyl phenylacetate (53.8 g, 0.291 mol) and dimethylformamide (50 mL). The reaction was heated to 90° C. for 1 hour, cooled to room temperature and then quenched into 1 N hydrochloric acid (1 L). This was then extracted with ethyl acetate (3×500 mL) and the combined organic layers were washed with water (2×500 mL), dried with magnesium sulfate, filtered and concentrated to give a red gum. Chromatographic purification on silica gel utilizing a gradient elution of hexanes to 30% ethyl acetate/hexanes gave the title compound (61.8 g, 47%). Recrystallization from ethyl acetate/hexanes gave white prisms: mp 158°–161° C.

Anal. Calc'd for C₂₉H₂₃NO₄: C, 77.5; H, 5.2; N, 3.1.

Found: C, 77.1; H, 5.2; N, 3.0.

PREPARATION C

Methyl 2-isopropyl-5-benzoxazole carboxylate

A solution of methyl 3-amino-4-hydroxybenzoate (5.00 g, 29.9 mmol), isobutyryl chloride (3.51 g, 32.9 mmol), triethylamine (3.33 g, 32.9 mmol), pyridinium p-toluenesulfonate (2.5 g, 10 mmol) and xylene (100 mL) was heated to reflux overnight and then cooled to room temperature. The reaction was diluted with ethyl acetate (100 mL) and washed with water (2×50 mL), dried with magnesium sulfate, filtered and concentrated to give the title compound (6.82 g, quantitative yield) as a brown oil. Also prepared by this method were:

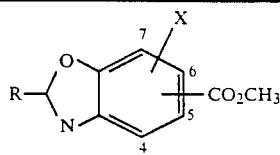

| R | X | Position of —CO₂CH₃ group | Yield % | m.p., °C. |
|---|---|---|---|---|
| C₆H₅— | H | 4 | 71 | 78-81 |
| CH₃— | H | 4 | 78 | 77-79 |
| C₆H₅— | H | 5 | 89 | 160-165 |
| CH₃— | H | 5 | 74 | — |
| C₆H₅— | H | 6 | 99 | 110-115 |
| CH₃— | H | 6 | 91 | 83-86 |
| C₆H₅— | H | 7 | 52 | — |
| CH₃— | H | 7 | 99 | — |
| p-CH₃C₆H₄— | H | 5 | 94 | — |
| (thienyl) | H | 5 | 66 | — |
| (furyl) | H | 5 | 46 | 158-160 |
| p-CF₃C₆H₄— | H | 5 | 34 | 155-157 |
| m-CH₃C₆H₄— | H | 5 | 93 | — |
| i-C₃H₇— | 7-CH₃O | 5 | 99 | — |
| (furyl) | 7-CH₃O | 5 | 53 | 124-126 |
| C₆H₅— | 7-CH₃O | 5 | 36 | 126-128 |
| (cyclohexyl) | 7-CH₃O | 5 | 75 | — |

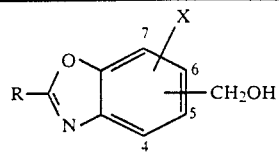

| R | X | Position of CH₂OH group | Yield % | m.p., °C. |
|---|---|---|---|---|
| CH₃— | H | 4 | 23 | 101-103 |
| C₆H₅— | H | 5 | 76 | — |
| CH₃— | H | 5 | 73 | — |
| C₆H₅— | H | 6 | 73 | — |
| CH₃— | H | 6 | 68 | 75-78 |
| C₆H₅— | H | 7 | 83 | — |
| CH₃— | H | 7 | 45 | — |
| p-CH₃C₆H₄ | H | 5 | 33 | — |
| (thienyl) | H | 5 | 56 | 146-149 |
| (furyl) | H | 5 | 13 | — |
| p-CF₃C₆H₄— | H | 5 | 96 | 173-175 |
| m-CH₃C₆H₄— | H | 5 | 99 | 142-145 |
| i-C₃H₇— | 7-CH₃O | 5 | 85 | — |
| (furyl) | 7-CH₃O | 5 | 93 | 158-160 |
| C₆H₅— | 7-CH₃O | 5 | 96 | 168-171 |
| (cyclohexyl) | 7-CH₃O | 5 | 98 | — |

PREPARATION D 2-isopropyl-5-benzoxazole methanol

To a solution of the product of preparation C (6.79 g, 29.9 mmol) and tetrahydrofuran (100 mL) was added lithium aluminumhydride (881 mg, 23.2 mmol) in one portion and the reaction stirred for 1.5 hours. The reaction was quenched by the sequential addition of water (0.9 mL), 15% sodium hydroxide solution (0.9 mL) and water (2.5 mL) and diluted with methylene chloride (100 mL). After 1 hour the suspension was filtered through a short pad of silica gel, dried with magnesium sulfate, filtered and concentrated to give the title compound (5.05 g, 88%) as an oil.

Also prepared by this method were:

PREPARATION E 2-isopropyl-5-benzoxazole methylbromide

To a solution of the product of preparation D (2.50 g, 13.1 mmol), triphenylphosphine (5.18 g, 19.7 mmol) and dimethylformamide (50 mL) was added carbon tetrabromide (6.54 g, 19.7 mmol). The reaction was stirred overnight and then poured into water (250 mL) and extracted with ethyl acetate (3×100 mL). The combined organic layers were dried with magnesium sulfate, filtered and concentrated. Chromatographic purification on silica gel with a gradient elution of hexanes to 10% ethyl acetate/hexanes gave the title compound (2.44 g, 73%) as a white solid: mp 62°-62° C.

Also prepared by this method were:

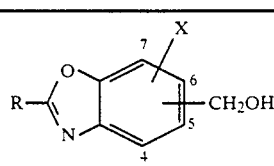

| R | X | Position of CH₂OH group | Yield % | m.p., °C. |
|---|---|---|---|---|
| C₆H₅— | H | 4 | 75 | 109-110 |

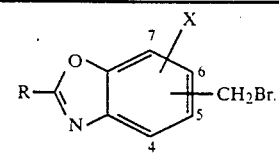

| R | X | Position of CH₂Br group | Yield % | m.p., °C. |
|---|---|---|---|---|
| C₆H₅— | H | 4 | 61 | 135-137 |
| CH₃— | H | 4 | 42 | 60-62 |

-continued

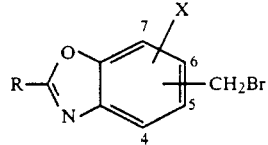

| R | X | Position of CH₂Br group | Yield % | m.p., °C. |
|---|---|---|---|---|
| C₆H₅— | H | 5 | 7 | — |
| CH₃— | H | 5 | 61 | 71–73 |
| C₆H₅— | H | 6 | 68 | 166–168 |
| CH₃— | H | 6 | 57 | — |
| C₆H₅— | H | 7 | 76 | 107–109 |
| CH₃— | H | 7 | 50 | 38–41 |
| p-CH₃C₆H₄ | H | 5 | 84 | 176–179 |
| (thienyl) | H | 5 | 87 | 161–162 |
| (furyl) | H | 5 | 45 | 133–136 |
| p-CF₃C₆H₄— | H | 5 | 62 | 155–157 |
| m-CH₃C₆H₄— | H | 5 | 82 | 159–160 |
| i-C₃H₇— | 7-CH₃O | 5 | 48 | 79–81 |
| (furyl) | 7-CH₃O | 5 | 84 | 167–169 |
| C₆H₅— | 7-CH₃O | 5 | 94 | 101–106 |
| (cyclohexyl) | 7-CH₃O | 5 | 70 | 75–77 |

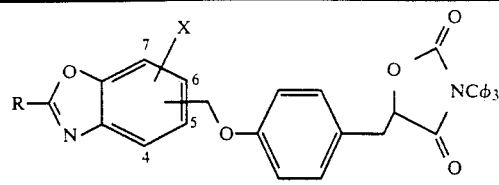

| R | Position of substitution | X | Yield % | m.p., °C. |
|---|---|---|---|---|
| C₆H₅— | 4 | H | 99 | — |
| CH₃— | 4 | H | 87 | 170–173 |
| C₆H₅— | 5 | H | 69 | — |
| CH₃ | 5 | H | 73 | 122–127 |
| C₆H₅ | 6 | H | 81 | — |
| CH₃— | 6 | H | 86 | — |
| C₆H₅— | 7 | H | 62 | 196–199 |
| CH₃— | 7 | H | 64 | 186–189 |
| p-CH₃C₆H₄— | 5 | H | 92 | — |
| (thienyl) | 5 | H | 38 | — |
| (furyl) | 5 | H | 97 | — |
| p-CF₃C₆H₄ | 5 | H | 93 | — |
| m-CH₃C₆H₄ | 5 | H | 95 | 188–190 |
| i-C₃H₇ | 5 | 7-CH₃O | 81 | — |
| (furyl) | 5 | 7-CH₃O | 50 | — |
| C₆H₅— | 5 | 7-CH₃O | 85 | — |
| (cyclohexyl) | 5 | 7-CH₃O | 93 | — |

PREPARATION F

3-Triphenylmethyl-5-(4-[2-i-propylbenzoxazol-5-ylmethoxy]benzyl)oxazolidine-2,4-dione To a suspension of sodium hydride (416 mg, 60% in oil, 10.4 mmol) in dimethylformamide (50 mL) was added the product of preparation B (4.24 g, 9.44 mmol). After the evolution of hydrogen had ceased, the product of preparation E (2.40 g, 9.44 mmol) was added in one portion and the reaction stirred overnight at room temperature. It was then poured into water (250 mL) and extracted with ethyl acetate (3×100 mL). The combined organic layers were dried with magnesium sulfate, filtered and concentrated to give an oil. Purification on silica gel utilizing a gradient elution of hexanes to 25% ethyl acetate in hexanes gave the title compound (4.85 g, 83%) as a white powder: mp 123°–125° C.

Also prepared by this method were:

PREPARATION G 4-(2-Isopropylbenzoxazol-5-ylmethoxy)benzaldehyde

To a 0° C. solution of the product of preparation D (1.41 g, 7.37 mmol), 4-hydroxybenzaldehyde (900 mg, 7.37 mmol) and triphenylphosphine (1.93 g, 7.37 mmol) in tetrahydrofuran was added diethylazodicarboxylate (1.60 g, 9.22 mmol) in a dropwise fashion. The reaction vessel was covered so as to exclude light and allowed to sit at room temperature overnight. The reaction was then filtered through celite and concentrated to a dark oil. Purification on silica gel utilizing a gradient elution of hexanes to 20% ethyl acetate/hexanes gave the title compound (500 mg, 23%) as a white solid: mp 86°–88° C.

Also prepared by this method was 4-(2-thien-2-ylbenzoxazol-5-ylmethoxy)benzaldehyde, m.p. 138°–140° C. (20% yield).

PREPARATION H 5-(4-[2-Isopropylbenzoxazol-5-ylmethoxy]phenylmethenyl)thiazolidine-2,4-dione A solution of the product of preparation G (480 mg, 1.62 mmol), thiazolidine-2,4-dione (381 mg, 3.25 mmol) and piperidine (60 mg) in ethanol was heated to reflux for 12 hours. The resulting yellow solid was collected by vacuum filtration and washed with ethanol to give the title compound (480 mg, 75%) as a yellow solid: mp 219°-221° C.

In a similar manner was prepared 5-(4-[2-thien-2-ylbenzoxazol-5-ylmethoxy]phenylmethenyl)thiazolidine-2,4-dione, m.p. 279-283 (79% yield).

I claim:
1. A compound of the formula

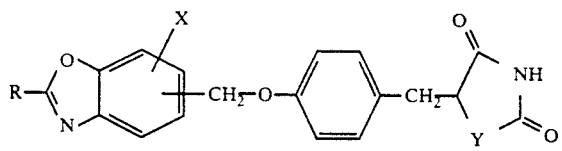

or a pharmaceutically acceptable base salt thereof wherein R is alkyl having one to six carbon atoms, cycloalkyl having three to six carbon atoms, furyl, thienyl, phenyl or substituted phenyl wherein said substituent is alkyl having one to three carbon atoms, methoxy, trifluoromethyl, chloro or fluoro; X is hydrogen, emthyl, methoxy, chloro or fluoro; and Y is O.

2. A compound of claim 1 of the formula

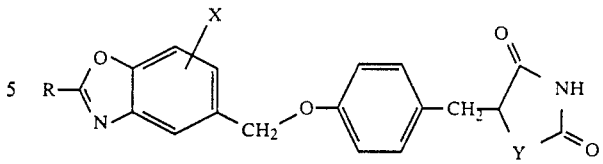

wherein X is hydrogen.

3. The compound of claim 2, wherein R is phenyl,
4. The compound of claim 2, wherein R is 2-thienyl.
5. The compound of claim 2, wherein R is 2-furyl.
6. The compound of claim 2, wherein R is i-propyl.
7. A pharmaceutical composition for use in a hyperglycemic or hyopercholesterolemic mammal which comprises a blood glucose or cholesterol lowering amount of a compound of claim 1 and a pharmaceutically acceptable carrier.
8. A method of lowering the blood glucose in a hyperglycemic mammal which comprises administering to said mammal a blood glucose lowering effective amount of a compound of claim 1.
9. A method of lowering the blood cholesterol in a hypercholesterolemic mammal which comprises administering to said mammal a blood cholesterol lowering effective amount of a compound of claim 1.

* * * * *